(12) United States Patent
Patolsky et al.

(10) Patent No.: US 9,228,991 B2
(45) Date of Patent: Jan. 5, 2016

(54) METHODS AND KITS FOR DETECTION OF DRUGS

(75) Inventors: Fernando Patolsky, Rehovot (IL); Michael Ioffe, Holon (IL); Eli Flaxer, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 105 days.

(21) Appl. No.: 13/991,983

(22) PCT Filed: Dec. 6, 2011

(86) PCT No.: PCT/IL2011/050041
§ 371 (c)(1),
(2), (4) Date: Aug. 1, 2013

(87) PCT Pub. No.: WO2012/077110
PCT Pub. Date: Jun. 14, 2012

(65) Prior Publication Data
US 2013/0329216 A1   Dec. 12, 2013

Related U.S. Application Data

(60) Provisional application No. 61/420,121, filed on Dec. 6, 2010.

(51) Int. Cl.
*G01N 21/00* (2006.01)
*G01N 33/14* (2006.01)
*G01N 21/49* (2006.01)
*G01N 21/59* (2006.01)

(52) U.S. Cl.
CPC ............... *G01N 33/14* (2013.01); *G01N 21/00* (2013.01); *G01N 21/49* (2013.01); *G01N 21/59* (2013.01); *G01N 33/146* (2013.01); *G01N 33/143* (2013.01)

(58) Field of Classification Search
CPC ...... G01N 21/59; G01N 33/14; G01N 33/143
USPC .................................... 356/51, 336–337, 436
See application file for complete search history.

(56) References Cited

U.S. PATENT DOCUMENTS

| | | | |
|---|---|---|---|
| 7,238,533 B1 | 7/2007 | Legge et al. | |
| 2002/0182600 A1* | 12/2002 | Smith | 435/6 |
| 2003/0026731 A1 | 2/2003 | Peter | |
| 2003/0044989 A1 | 3/2003 | Guerra et al. | |
| 2003/0224474 A1* | 12/2003 | Litman | 435/28 |

(Continued)

FOREIGN PATENT DOCUMENTS

| | | |
|---|---|---|
| CN | 1487294 A | 4/2004 |
| CN | 1609610 A | 4/2005 |

(Continued)

OTHER PUBLICATIONS

Bishop et al., "Micellar Electrokinetic Chromatographic Screening Method for Common Sexual Assault Drugs Administered in Beverages," *Forensic Science International*, vol. 141, pp. 7-15.

(Continued)

*Primary Examiner* — Gregory J Toatley
*Assistant Examiner* — Iyabo S Alli
(74) *Attorney, Agent, or Firm* — Oliff PLC

(57) ABSTRACT

The present invention discloses a method for determining the presence of a drug or drug mixture in a liquid medium such as a beverage.

20 Claims, 6 Drawing Sheets

(56) References Cited

U.S. PATENT DOCUMENTS

| | | |
|---|---|---|
| 2004/0076546 A1 | 4/2004 | Bissett |
| 2004/0146429 A1 | 7/2004 | Guerra et al. |
| 2005/0077476 A1* | 4/2005 | Poteet et al. ............... 250/461.1 |
| 2009/0266290 A1 | 10/2009 | Sliwa et al. |
| 2010/0041078 A1 | 2/2010 | Bendinskas et al. |
| 2010/0081188 A1 | 4/2010 | Campbell et al. |
| 2011/0039346 A1 | 2/2011 | Bradley et al. |
| 2011/0195507 A1 | 8/2011 | Dancer |
| 2011/0293799 A1 | 12/2011 | Thomas |

FOREIGN PATENT DOCUMENTS

| | | |
|---|---|---|
| CN | 101603954 A | 12/2009 |
| GB | 2 410 087 A | 7/2005 |
| GB | 2 418 248 A | 3/2006 |
| GB | 2 425 350 A | 10/2006 |
| GB | 2 447 899 A | 10/2008 |
| GB | 2 453 448 A | 4/2009 |
| JP | 2003-520942 A | 7/2003 |
| JP | 2009-523242 A | 6/2009 |
| WO | WO 2005/059541 A1 | 6/2005 |
| WO | WO 2005/088297 A1 | 9/2005 |
| WO | WO 2006/018619 A1 | 2/2006 |
| WO | WO 2006/131225 A1 | 12/2006 |
| WO | WO 2007/056699 A3 | 5/2007 |
| WO | 2010/124999 A1 | 11/2010 |
| WO | 2012/077110 A2 | 6/2012 |

OTHER PUBLICATIONS

Blackledge et al., "The Identification of GHB," *Microgram*, Jul. 1991, vol. 24, No. 7, pp. 173-179.

Kintz et al., "Window of Detection of γ-Hydroxybutyrate in Blood and Saliva," *Clinical Chemistry*, 2001, vol. 47, No. 11, pp. 2033-2034.

Hennessy et al., "The Reactivity of Gamma-Hydroxybutyric Acid (GHB) and Gamma-Butyrolactone (GBL) in Alcoholic Solutions," *Journal of Forensic Sciences*, vol. 49, No. 6, pp. 1-10.

Meyers et al., "A Study of the Effectiveness of Commercially Available Drink Test Coasters for the Detection of "Date Rape" Drugs in Beverages," *Journal of Analytical Toxicology*, 2004, vol. 28, pp. 685-688.

Jul. 5, 2012 International Search Report issued in International Application No. PCT/IL2011/050041.

Xu, "Determination of Ketamine in Drink by Gas Chromatography with Bore Capilly Column," *Chemical Research*, Dec. 2001, pp. 45-46, vol. 12, No. 4 (with English abstract).

Ning et al., "Determination of caffeine in beverages by HPLC," *Chinese Journal of Health Laboratory Technology*, Mar. 2009, pp. 506-562, vol. 19, No. 3 (with English abstract).

Elliott et al., "The presence of gamma-hydroxybutyric acid (GHB) and gamma-butyrolactone (GBL) in alcoholic and non-alcoholic beverages," *Forensic Science International*, 2005, pp. 289-292, vol. 151.

\* cited by examiner

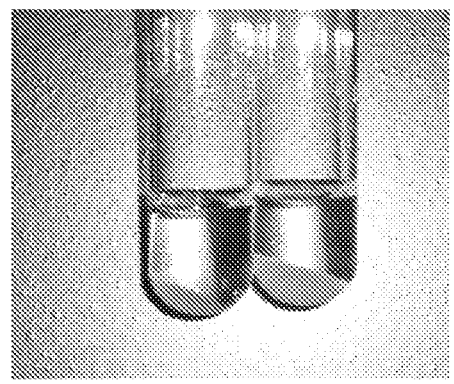
Fig. 3
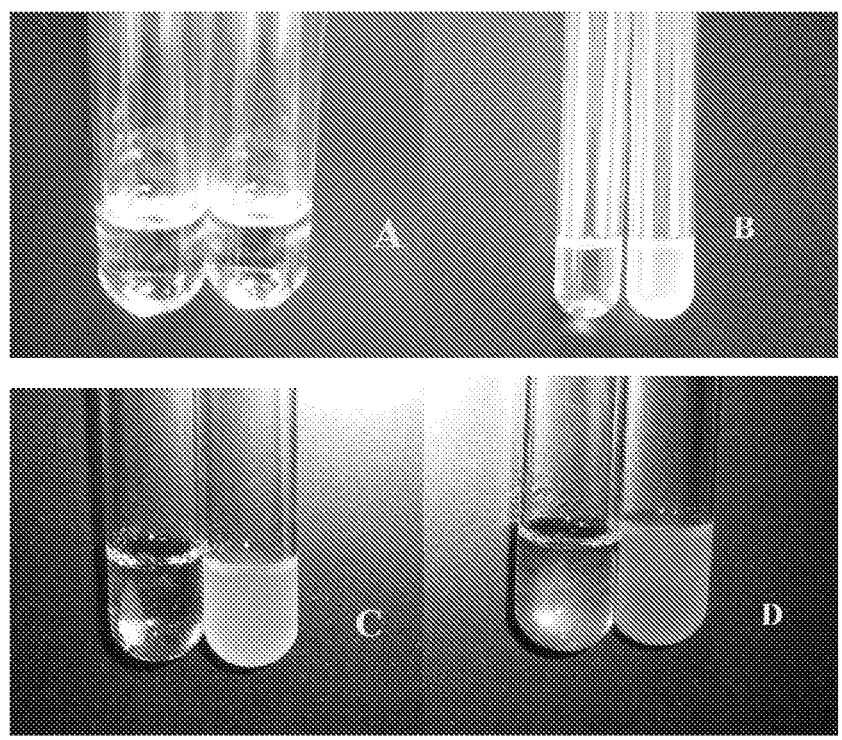
Figs. 4A-D

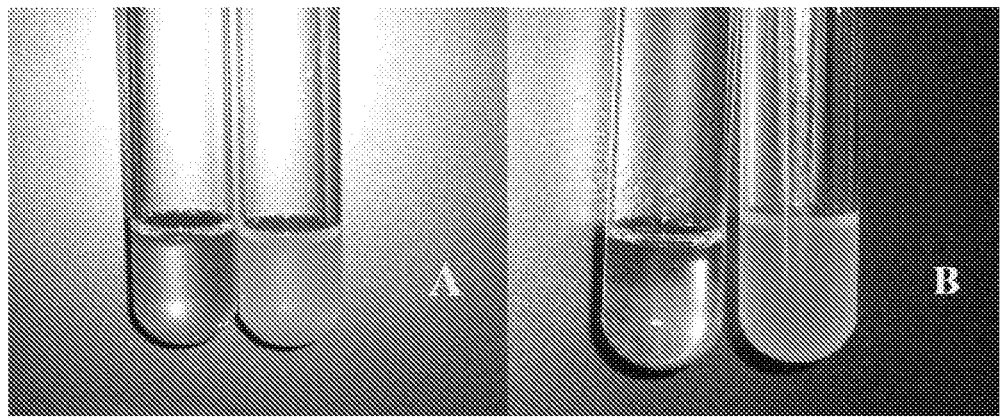
Figs. 5A-B
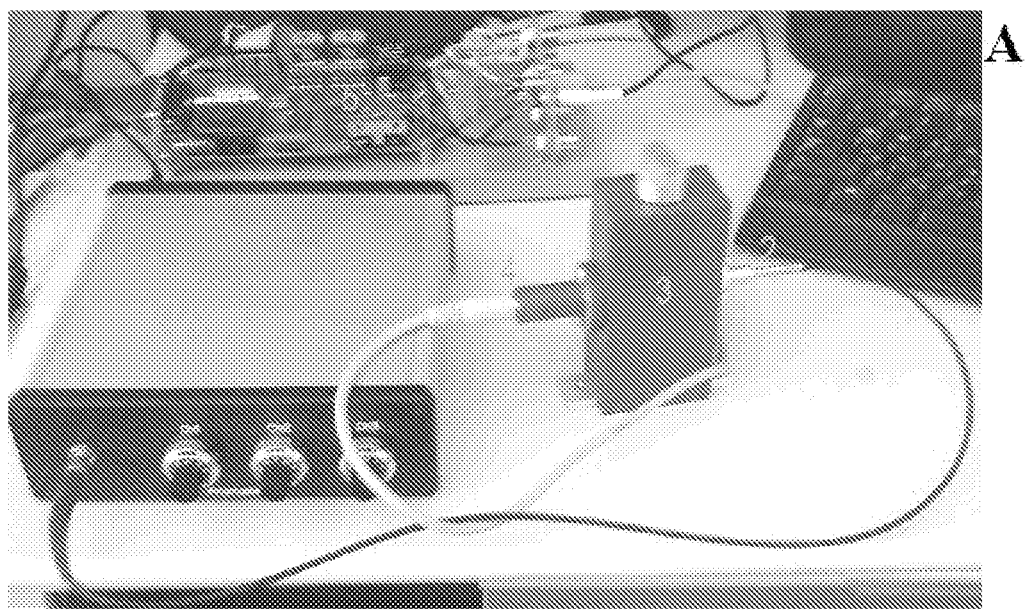
Fig. 6A

METHODS AND KITS FOR DETECTION OF DRUGS

FIELD OF THE INVENTION

This invention relates generally to methods and kits for the detection of various drugs, such as date-rape drugs, in alcoholic and non-alcoholic beverages.

BACKGROUND OF THE INVENTION

Due to the major social problems associated with narcotic abuse, the detection of illicit drugs has become an area of major research. Several broad categories of detection techniques are generally known, including imaging methods, such as x-ray based technologies, the use of trained canines, colorimetric tests and trace chemical detection methods utilizing various "sniffer" technologies. The last category involves indirect detection of a drug by collecting and analyzing minute quantities of vapor or particle contamination. Several technologies have been developed for this type of application, of which ion mobility spectrometry (IMS) is perhaps the most widely utilized.

Drug-facilitated sexual assaults has also become an increasing and concerning problem throughout the world. Drugs used to facilitate rape may have sedative, hypnotic, dissociative, and/or amnesiac effects, and can be readily added to a food or drink without the victim's knowledge. Existing field tests for the so-called "date rape" drugs are not, at best, entirely reliable and sensitive, and cannot be used on all types of drinks due to intrinsic experimental limitations [1-6]. Also, interpretation of the obtained results is often problematic under real-life conditions.

Besides alcohol itself, the most known date-rape drugs are gamma-hydroxybutyrate (GHB), and ketamine. Gamma-hydroxybutyrate (GHB), an 'easy-to-make' small endogenous polar compound ($C_4H_8O_3$), has become the rapist's drug of choice as it has no taste, color or odor, making it hard to detect in a drink GHB is naturally found in trace amounts throughout the human body and is chemically very similar to the neurotransmitter γ-amino butyric acid (GABA).

Initially utilized as an anesthetic, GHB is now employed in narcolepsy, cataplexy and alcohol/opiate withdrawal treatments. However, it is also abused as a recreational drug for its various "desired" effects: euphoria, hallucinations and aphrodisiac. Yet, its adverse effects are all real; aggressive behavior, nausea/vomiting, hallucinations, bradycardia, loss of consciousness, respiratory failure, memory loss and potential death at high doses. When used as a rape-assisting drug, GHB incapacitates the victims, which are usually wrongly diagnosed as "drunk".

GHB would not be detected on a general drug screening and its detection is only available in specialist laboratories. A key concern with GHB is that there is only a small difference between the dose which leaves the victim unconscious and a dose that may lead to death. A heavy dose is approximately 2.5 grams of GHB. An extra 0.25 grams could be the difference between euphoria and unconsciousness. A dangerous overdose can occur with as little as two grams depending on body weight and the individual's metabolism. Some GHB overdoses lead to unconsciousness, vomiting and a loss of the gag reflex, putting the victim in grave danger of aspiration and death.

Despite the rapid increase in the number of cases in which GHB, and to that extent also ketamine, have been used for abuse, the available methods for detecting the presence of such drugs, particularly GHB, are insensitive, cumbersome and not reliable in detecting these drugs at the required concentrations, in a broad range of alcoholic and non-alcoholic beverages and under real-life conditions. Thus, the development of simple, sensitive and reliable methods for the rapid field detection of 'date-rape' drugs in a broad variety of beverages is required.

REFERENCES

[1] Meyers, J. E.; Almirall, J. R., A study of the effectiveness of commercially available drink test coasters for the detection of "date rape" drugs in beverages. *J. Anal. Toxicol.*, 2004, 28(8), 685-688.

[2] Walker L. Identification of the potassium salt of gamma-hydroxybutyric acid (GHB). *J. Clan. Lab. Invest. Chem. Assoc.*, 1999, 9(1), 17-18.

[3] Bommarito, C.; Analytical profile of gamma-hydroxybutyric acid (GHB). *J. Clan. Lab. Invest. Chem. Assoc.*, 1993, 3, 10-12.

[4] Blackledge, R. D.; Miller, M. D. The identification of GHB. *Microgram* 1991, 24, 172-179.

[5] Hennessy, S. A.; Moane, S. M.; McDermott, S. D. The reactivity of gamma-hydroxybutyric acid (GHB) and gamma-butyrolactone (GBL) in alcoholic solutions. *J. Forensic Sci.*, 2004, 49(6), 1220-1229.

[6] Meyers, J. E.; Almirall, J. R., A study of the effectiveness of commercially available drink test coasters for the detection of "date rape" drugs in beverages. *J. Anal. Toxicol.*, 2004, 28(8), 685-688.

SUMMARY OF THE INVENTION

Herein are disclosed methods and kits for the rapid, reliable and sensitive detection of a variety of drugs directly from a broad range of alcoholic and non-alcoholic beverages. The method of the invention does not require the use of enzymatic reagents or the creation of a chemical reaction as means for detection, and may be used on-spot without necessitating complex analysis or prior scientific understanding. The method of the invention is generally based on a solvent/anti-solvent method, by which the addition to a reference solution (the so-called solvent mixture) of a small volume of a drug-containing sample leads to a change in an optical parameter (e.g., transmittance, scattering) associated with and predetermined for the drug-free reference solution. The change in the optical parameter is assumed not to result from the medium in which the drug is dissolved, e.g., beverage, but rather from the full or partial insolubility of the drug in the reference solution. The insolubility of the drug in the reference solution thus results in the formation of turbidity or a colloidal state or a multiphase state and thus in a change in the optical parameter predetermined for the reference solution free of the drug.

The change in the optical parameter indicates the presence of a suspected drug in the beverage, and may be detected by the naked eye or by any optical means. The ability to determine the presence or absence of a drug in a sample, e.g., beverage, in accordance with the method of the invention, is not affected by factors such as the color, pH or density of the sample under examination.

Thus, in a first aspect of the invention, there is provided a method for determining the presence/absence of a drug in a liquid medium, the method comprising:

providing one or more solvent mixture(s) having a predetermined optical parameter, said solvent mixture being capable of undergoing a change in at least one optical parameter in the presence of a drug; and contacting said solvent mixture with a liquid medium suspected of containing an amount of said drug;

whereby a change in the predetermined optical parameter of said solvent mixture following the contacting thereof with said liquid medium suspected of containing an amount of said drug, indicates the presence of said drug in said liquid medium.

In some embodiments, the medium is allowed to mix (e.g., by shaking) with said solvent mixture sample so as to induce or hasten the formation of, e.g., turbidity, and subsequently a change in said at least one optical parameter.

In further embodiments, prior to the addition of the liquid medium sample into the solvent mixture, the liquid medium sample is measured for determining the at least one optical parameter for comparing thereof to that obtained following contact with the solvent mixture. Thus, the method of the invention may comprise:

providing one or more solvent mixture(s) having a predetermined optical parameter, said solvent mixture being capable of undergoing a change in at least one optical parameter in the presence of a drug;

obtaining a sample of a liquid medium suspected of containing a drug and optionally measuring at least one optical parameter thereof;

contacting said solvent mixture with a liquid medium sample;

whereby a change in the predetermined optical parameter of said solvent mixture following the contacting thereof with said liquid medium suspected of containing an amount of said drug, or a change in the predetermined optical parameter of said liquid medium sample following contacting thereof with said solvent mixture, indicates the presence of said drug in said liquid medium.

The method disclosed herein can be used for detecting any kind of drug, or mixture of drugs, contained in a liquid medium, e.g., in a beverage. In some embodiments the drug is a "recreational drug" or an "illicit drug", i.e., any substance or chemical, which may be synthetic or naturally obtained. The drug, the presence of which is to be detected in accordance with the present invention, may be a psychoactive drug, such as, a depressant, an antihistamine, an analgesic, a tranquilizer, a hallucinogen, a psychedelic, a deliriant and a stimulant.

In some non-limiting embodiments, the drug is allobarbital, or amobarbital, or aprobarbital, or alphenal, or barbital, or brallobarbital, or phenobarbital, alprazolam, or bretazenil, or bromazepam, or brotizolam, or chlordiazepoxide, or cinolazepam, or clonazepam, or clorazepate, or clotiazepam, or cloxazolam, or delorazepam, or diazepam, or estazolam, or etizolam, or flurazepam, or flutoprazepam, or halazepam, or ketazolam, or loprazolam, or lorazepam, or lormetazepam, or medazepam, or midazolam, or nimetazepam, or nitrazepam, or nordazepam, or oxazepam, or phenazepam, or pinazepam, or prazepam, or premazepam, or quazepam, or temazepam, or tetrazepam, or triazolam, ipratropium bromide (Atrovent), or oxitropium bromide (Oxivent), or tiotropium (Spiriva), or glycopyrrolate (Robinul), or oxybutinin (Ditropan, Lyrinel XL), or tolterodine (Detrol), or azelastine, or cetirizine, or cyclizine, or chlorpheniramine, or clemastine, or desloratadine, or dexchlorpheniramine, or dimenhydrinate (most commonly used as an antiemetic), or dimetindene, or diphenhydramine (benadryl), or doxylamine, or ebastine, or embramine, or fexofenadine, or levocetirizine, or loratadine, or meclozine, or olopatadine, or pheniramine, or promethazine, or quetiapine, or rupatadine, or cimetidine, or famotidine, or lafutidine, or nizatidine, or ranitidine, or roxatidine, paracetamol, or the non-steroidal anti-inflammatory drugs (NSAIDs) such as the salicylates, or opioid drugs such as hydrocodone or codeine or heroin or oxycodone.

Some further examples include barbiturates, or benzodiazepines, or nonbenzodiazepines, or carisoprodol (soma), or chloral hydrate, or diethyl ether, or ethchlorvynol, or gabapentin (neurontin), or gamma-butyrolactone (GBL) or gamma-hydroxybutyrate (GHB), or glutethimide (doriden), or kava, or kavalactones or meprobamate (miltown), or methaqualone, or pregabalin (lyrica), or propofol (diprivan), or theanine or valerian, or atropine, or dimenhydrinate (Dramamine), or diphenhydramine, or hyoscyamine, or scopolamine, or myristicin, or ibotenic acid, or muscimol, or dextromethorphan, or dextromethorphan, or chlorpheniramine, or ketamine, or methoxetamine, or phencyclidine or nitrous oxide, or phenethylamines, or MDMA, or mescaline, or tryptamines, or alpha-methyltryptamine, or bufotenin, or dimethyltryptamine, or lysergic acid amide, or lysergic acid diethylamide (LSD), or psilocin, or psilocybin, or ibogaine, or salvinorin A, or sympathomimetics (catecholaminergics), or Entactogens, or arecoline, or rauwolscine, or yohimbine.

In some embodiments, the drug is caffeine or tetrahydrocannabinol (THC) or hydrocodone, or oxycodone, or morphine, or diacetylmorphine (heroin), or cocaine, or lidocaine, or novocaine.

In some embodiments, said drug is at least one drug selected from GHB (or derivatives or prodrugs of GHB, e.g., GBL), and ketamine.

The "liquid medium" refers to the beverage or to any liquid in which the drug is not a desired component thereof. The liquid medium, e.g., beverage, may be water, an aqueous medium, or an alcoholic medium, e.g., ethanol, ethanolic solutions or any other organic solvent. As used herein, the liquid medium sample is an aliquot of a desired volume which is removed from said, e.g., beverage and added into the solvent mixture in accordance with the invention.

In some embodiments, the liquid medium is a drink or a beverage. In other embodiments, the liquid medium is water, or a beverage containing water, or an alcoholic beverage or a non-alcoholic beverage or a soft drink, or a fruit juice, or a hot beverage. In some embodiments, the liquid medium is an alcoholic beverage, e.g., a fermented beverage such as wine, bear and ale. In some embodiments, the fermented beverage ale selected from barleywine, bitter ale, mild ale, pale ale, porter, stout, cask ale, sand tock ale. In some embodiments, the fermented beverages is beer selected from fruit beer, lager beer, bock, dry beer, maerzen/oktoberfest beer, pilsener, schwarzbier, sahti, small beer, wheat beer, witbier white beer and hefeweizen.

In some embodiments, the fermented beverages is wine selected from fruit wine, table wine, sangria, sparkling wine, champagne, fortified wine, port, madeira, marsala, sherry, vermouth and vinsanto.

In some embodiments, the liquid medium is a distilled beverage. The distilled beverages may be selected amongst spirits, such as absinthe, akvavit, arak, arrack, baijiu, cachaca, gin, damson gin, sloe gin, horilka, kaoliang, maotai, mezcal, neutral grain spirit, ogogoro, ouzo, palinka, pisco, rakia, slivovitz, rum, soju, tequila, Vodka, metaxa, whisky (bourbon, scotch, tennessee whiskey) and brandy (armagnac, cognac, fruit brandy, damassine, himbeergeist, kirsch, poire williams, williamine, zwetschgenwasser).

In some embodiments, the distilled beverage is a liqueur. The liqueur may be selected from berry liqueurs, coffee liqueurs, cream liqueurs, flower liqueurs, fruit liqueurs, herbal liqueurs (such as anise-flavored liqueurs), honey liqueurs, nut-flavored liqueurs, whisky liqueurs and others.

In some embodiments, the alcoholic beverage is a cocktail. The cocktail may be selected from cocktails with absinthe, cocktails with beer, cocktails with brandy, cognac or cocktails with cachaca, cocktails with gin, cocktails with rum, cocktails with sake, cocktails with tequila, cocktails with vodka, cocktails with whiskey, rye or bourbon, cocktails with wine, sparkling wine, or port, and cocktails with a liqueur.

In some embodiments, the liquid medium is a non-alcoholic beverage. In some embodiments, the non-alcoholic beverage is a non-alcoholic cocktail (such as a cocktail of ginger ale and orange juice), aguas frescas, aguapanela, almdudler, apfelschorle, atole, ayran, babycino, baesuk, bandrek, bandung, barley water, birch sap, bread drink, cendol, chalap, champurrado, champús, chass, cholado, chai, coffee, egg nog, elderflower cordial, falooda, garapa, ginger tea, Hawaiian punch, horchata, hot chocolate, hwachae, jindallae hwachae, kombucha, lassi, licuado, mattha, mazamorra, milkshake, mocochinchi, mote con huesillo, nectar, orange drink or orange soft drink, peanut milk, peanut punch, sherbet, shikanjvi, smoothie, subak hwachae, sujeonggwa, switchel, tea, thadal, yuja hwachae and cola.

The liquid medium may comprise one or more additional agents such as colorants, taste modifying agents, and others.

The solvent mixture capable of undergoing at least one optical change in the presence of said drug is a predetermined mixture for a particular drug/family of drugs (based on chemical structure or solubility). The mixture, prior to the addition of the liquid medium sample may be a single solvent, e.g., acetonitrile, ethanol, or a mixture of two or more solvents. The mixture in some embodiments is a solvent/antisolvent mixture comprising at least one solvent which solubilizes the drug and at least one other solvent, the so-called antisolvent, in which the drug is insoluble. Once the drug is added to said solvent mixture, at least one measurable optical parameter of the solvent mixture is altered. Such a change is not affected by the liquid medium itself. Thus, any change in the optical parameter may be attributed to the presence of the drug.

In other embodiments, the solvent mixture comprises a single solvent, e.g., acetonitrile, which upon contact with at least one component of said liquid medium sample (one or more solvents) produces a solvent/antisolvent medium in which the drug (also contained in the liquid medium solvent) is partially or fully insoluble.

In some embodiments, the drug is GHB and the solvent mixture comprises acetonitrile. In some embodiments, the drug is GHB and the solvent mixture comprises ethanol. In further embodiments, where the drug is GHB, the solvent mixture is ethanol:acetonitrile. In some embodiments, the drug is GHB and the solvent mixture is acetonitrile (100%), ethanol (100%), or ethanol:acetonitrile (1:1).

In some embodiments, the drug is ketamine and the solvent mixture comprises isopropanol and/or glycerine and/or NaOH. In some embodiments, the drug is ketamine and the solvent mixture comprises isopropanol and glycerine and NaOH. In some embodiments, the drug is ketamine and the solvent mixture comprises isopropanol:glycerine:NaOH (1:10:0.25).

The detection of the drug is done by observing a change in an optical parameter which is associated with the presence of the drug. The change of the optical parameter is a change in an optical parameter of the solvent mixture when in contact with the drug, as compared to a solvent mixture without the drug or with the liquid medium, e.g., beverage free of the drug.

The at least one optical property may be associated with light transmission.

In some embodiments, the measured optical parameter is transmittance (or optical density). In some embodiments, the measured optical parameter is scattering.

The invention also provides a device for determining the presence/absence of a drug in a liquid medium, the device comprising at least one optionally detachable testing cell (in a testing cell assembly) for holding a solvent mixture, means for withdrawing a sample (a beverage sample) suspected of containing a drug into said at least one testing cell, and a detection unit for detecting a change in at least one optical parameter of the liquid in said testing cell following contact with the sample.

As may be understood, the measuring of the optical parameter, subsequent to the addition of the sample, may be carried out by a detection unit which is not part of the detection device.

As stated above, the testing cell(s) or assembly holding said cell(s) may be constructed for optional detachment from said device. The assembly may be detached and disposed of after a beverage has been tested, and subsequently replaced by another such testing cell or assembly already containing one or more, in separate cells, solvent mixtures in accordance with the invention.

A general scheme of a device for determining the presence of a drug in a liquid medium according to the invention is presented in FIG. 1. The device of the invention 1 is provided with a light source 20. Light beam from said light source 20 passes through the testing cell 30 contained in a sample holder 40, which according to some embodiments of the invention, may contain more than 1 testing cell, namely-2, 3, 4, 5, or more testing cells (multicell). The testing cell 30 comprises the solvent mixture and a sample liquid medium which drug content is to be determined. The testing cell(s) 30 has an inlet (not shown) through which a sample, e.g., beverage, may be delivered by any means known in the art. A photodetector 50 positioned, in some embodiments, at the optical path or at an angle (perpendicular) thereto, measures the transmitted light or the scattered light after passing through the sample in said testing cell.

The device of the invention, in accordance with some of its designs may operate in the transmittance measurement mode (mode I), whereby the photodetector is mounted along the incident beam axis. In the alternative scattering measurement mode (mode II) the photodetector may be mounted perpendicular to the incident beam axis.

The photodetector 50 is connected to a data processing device 60, which processes the data and compares it to a reference value previously obtained for the solvent mixture in said one or more testing cell(s) 30. In accordance with the invention, if a drug is presence in the liquid medium, e.g., beverage, a warning system 70 will be switched on. The indication system may be in the form of any visual or audio display.

In some embodiments, the device may further comprise a transmission unit capable of transmitting (e.g., by radio frequency) a warning signal to a receiver mounted in a cellular telephone, computer, etc. The receiver may be at the location where the method of the invention is carried out or at a remote location.

The device may be designed for multiple and consecutive uses. Additionally, or alternatively, the device may be designed for multiple simultaneous uses.

The device for determining the presence of a drug in a liquid medium comprises a sample holder, a light source, a light detector, and a data processing device. The sample holder may be connected to a pumping liquid component, and may comprise a membrane or semi-permeable membrane allowing passage of a liquid medium to a reservoir containing the solvent mixture (solvent/antisolvent mixture).

The testing cell may be a multicell assembly to permit simultaneous testing of a drug containing liquid medium with multiple solvent mixtures, wherein each solvent mixture being contained in a different cell of the multicell assembly.

In some embodiments, the number of cells in the multicell assembly is at least two cells. In some embodiments, the number of cells is 10 or more. In further embodiments, the number of cells is 1 or 2 or 3 or 4 or 5 or 6 or 7 or 8 or 9 or 10 cells.

The amount of liquid medium that needs to be withdrawn, namely the size of the tested sample is minimal. In some embodiments, the sampling amount may be greater than 0.1 µL. In some embodiments, the sampling amount is greater than 0.1 µL, greater than 1 µL, greater than 100 µL, or greater than 1 mL. In some embodiments, the sampling amount of the tested liquid medium is in the range of between 1 and 100 µL. In some embodiments, the sampling amount of the tested liquid medium is in the range of between 100 µL and 1 mL.

The solvent mixture employed in a device according to the invention should be adequate to permit a change in an observed (tested) optical parameter. In some embodiments, the sampling amount is greater than 0.1 µL, greater than 1 µL, greater than 100 µL, or greater than 1 mL. In some embodiments, the sampling amount of the tested liquid medium is in the range of between 1 and 100 µL. In some embodiments, the sampling amount of the tested liquid medium is in the range of between 100 µL and 1 mL.

In some embodiments, the device further comprises a dispensing system, e.g., in the form of a pipettor (one or more), or micropipettor (one or more).

The light source unit may comprise one or more light sources. In some embodiments, the light source unit comprises between 2 and 10 light sources. In some embodiments, the light source unit comprises 1 or 2 or 3 or 4 or 5 or 6 or 7 or 8 or 9 or 10 light sources.

In some embodiments, the light source irradiation may be in the Infra Red (IR) (including NIR-IR, FAR-IR) regime. In other embodiments, the light source irradiation may be at 450 nm and/or 560 nm and/or 750 nm.

The light source employed for detecting the optical change may be any light source such as a laser, such as Ar laser, He—Ne laser, and dye laser, light lamp such as a mercury lamp, a light emitting diode such as solid-state diode, organic light-emitting diode, and other available light sources.

The light detector unit may comprise any one or more light detector(s). In some embodiments, the light detector is a photodiode, a photoresistor, an avelanche photodiode (APD), a charge-coupled device (CCD), a light dependent resistor (LDR), a phototube or a photomultiplier tube (PMT). In some embodiments, the detector is a photodiode.

The indication system may comprise of an indicator which alarms the presence of a drug in the liquid medium (sample). The indication system may comprise one or more indicator(s), which may or may not be drug specific, which may be visualized (light bulb, LED) or an audio device.

The device of the invention can be attached to or incorporated into an article which may be a liquid medium carrier, a glass of beverage, a cup, a bowl, a dish, a straw, a beverage stirring bar, a cutlery, a cocktail napkin, a beverage coaster, a placemat, a menu, a personal card or a pen.

Also provided is a kit for carrying out the detection method of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3 demonstrates GHB precipitation in acetonitrille (left) and pure ethanol (right).

FIGS. 4A-D depict the visual results of the acetonitrile anti-solvent solution, before and after the addition of a clean drink sample and a GHB-spiked sample. FIG. 4A depicts an antisolvent prior to sample addition, FIG. 4B depicts the visual result after the addition of a clean Finlandia vodka sample (left) and a GHB-spiked Finlandia vodka (right), FIG. 4C depicts the visual result after the addition of a clean Red label whiskey sample (left) and a GHB-spiked red Label whiskey (right), and FIG. 4D depicts the visual result after the addition of a clean Keglevich vodka sample (left) and a GHB-spiked Keglevich (right).

FIGS. 5A-B depict the visual results of the ethanol anti-solvent solution, after the addition of a clean drink sample and a GHB-spiked sample. FIG. 5A depicts the visual result after the addition of a clean Tavor red wine sample (left) and a GHB-spiked Tavor red wine (right), FIG. 5B depicts the visual result after the addition of a clean chardonnay white Tavor sample (left) and a GHB-spiked chardonnay white Tavor (right).

FIGS. 6A-C depict an experimental system, that was constructed for carrying out the diagnostic method of the invention and the results obtained in a GHB-detecting experiment. FIG. 6A depicts the experimental system. 1-Light source, 2-fibre-optic wire, 3-tube holder, 4-photodiode, and 5-data card, FIG. 6B depicts the optical curves obtained from tests performed on a clean vodka sample, curve a, and on GHB-spiked vodka sample, curve b, employing a device according to the invention, FIG. 6C is a representation of the signal change upon addition of different beverages with different GHB concentrations into a tube, containing antisolvent agent. Control is taken as 0 change. GHB concentrations are those in the tested beverages.

FIG. 7A is a representative graph of the change in the signal, according to the ketamine-dosage response of a beverage in the light-scattering test, FIG. 7B is a representation of the signal change upon addition different concentrations of ketamine into different beverages. Control is taken as 0 change. Ketamine concentrations are those in the tested beverage.

DETAILED DESCRIPTION OF EMBODIMENTS

The large diversity of alcoholic and non-alcoholic beverages and their mixtures makes the detection of chemical drugs spiked into these liquid samples extremely challenging. Extreme pH differences, colored beverages, low concentration of drug spiked into the beverages and additional numerous factors limit the usability and reliability of current methodologies based on the use of enzymes as detecting agents and visual color development as detection means.

Thus, finding new simple and generic approaches for the detection of drugs-spiked beverages is of great importance for the prevention of drug-facilitated assaults and forensic scenarios.

Here, describe are the developments of an extremely simple, fast, sensitive and low-cost approach for the sensing of several of the most abundant 'date-rape' drugs used these days in a broad spectrum of alcoholic and non-alcoholic beverages, as well as their mixtures.

Figure 1:
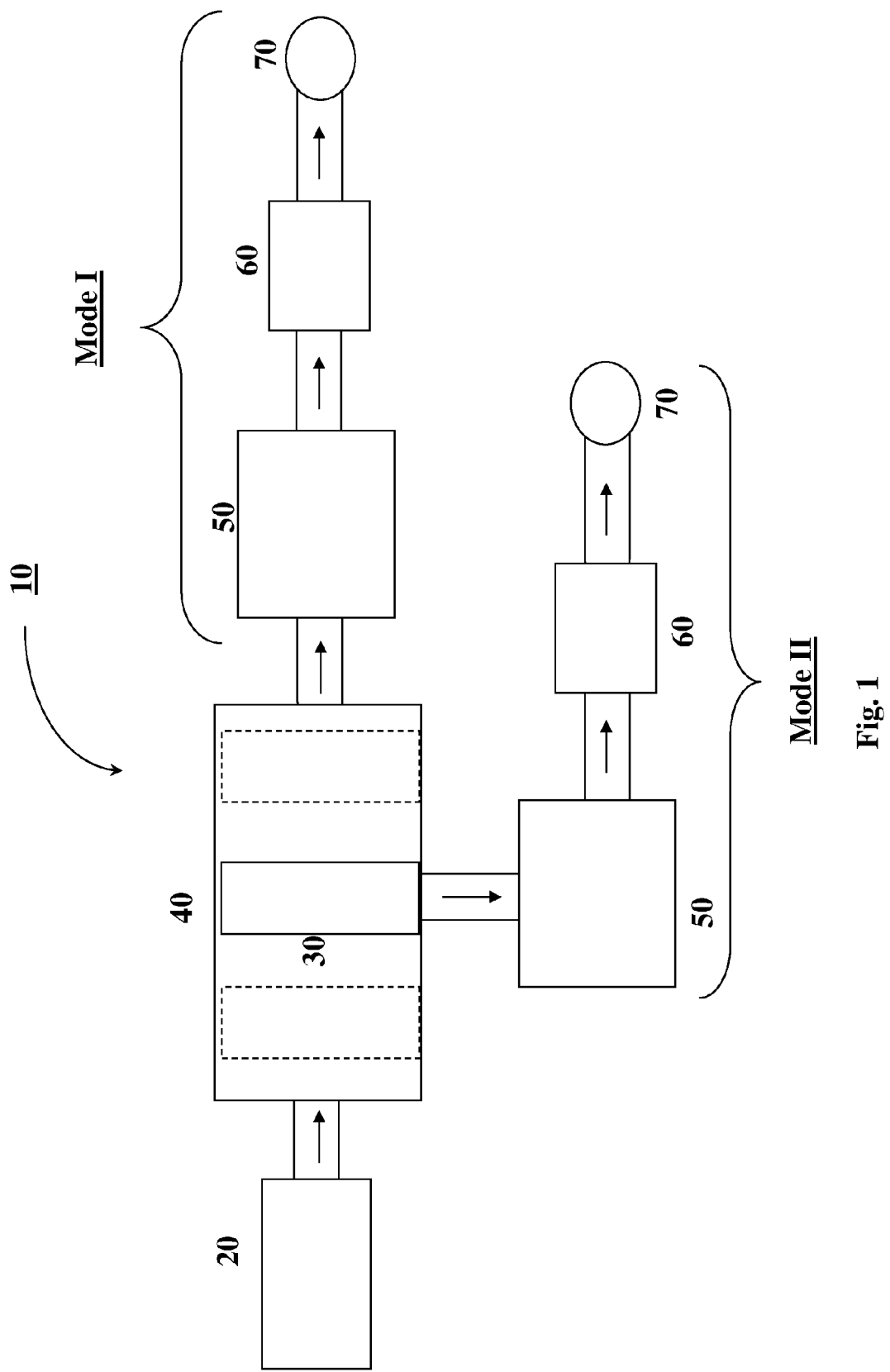
FIG. 1 is a general schematic representation of a device for carrying out a process according to the present invention.
Figure 2:
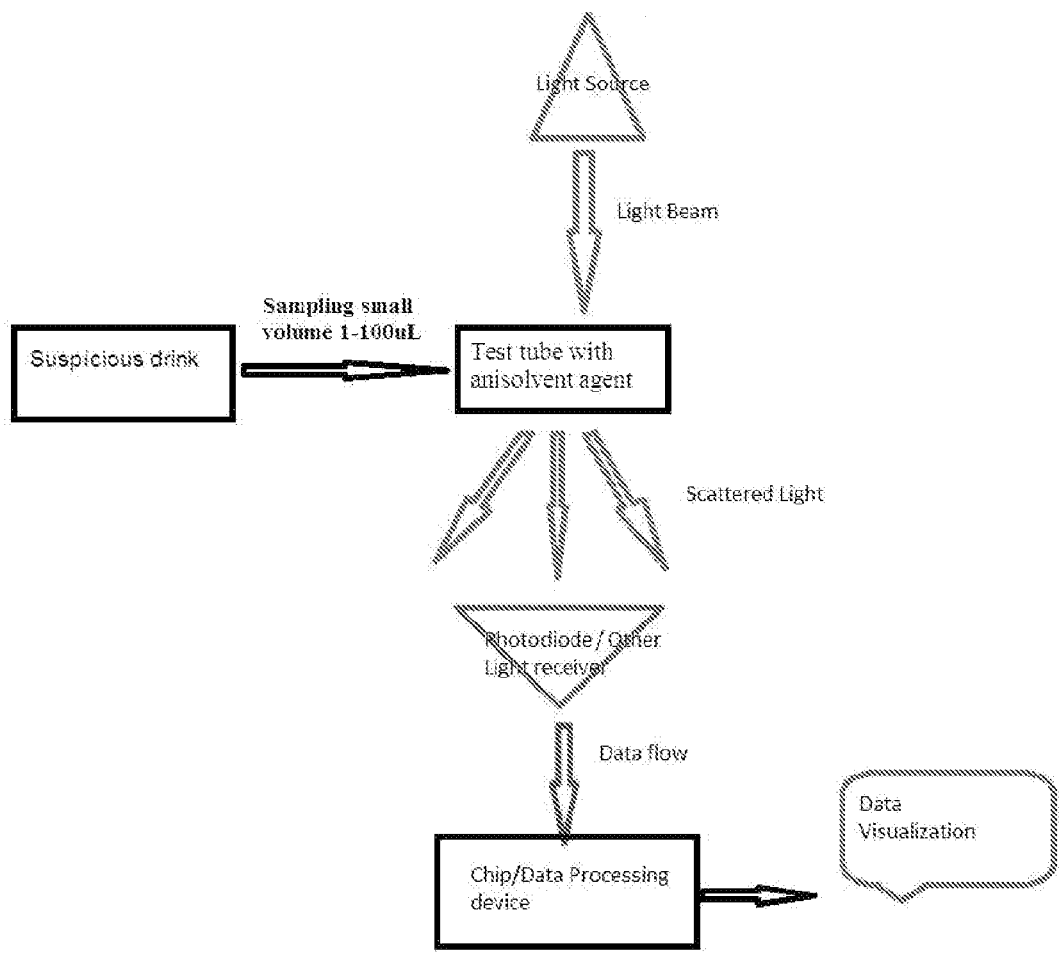
FIG. 2 is a general schematic representation of the solvent/anti-solvent optical detection approach.

The general detection scheme is based on the chemical principle: (i) firstly finding a solvent or solvent mixture, the so called 'anti-solvent', in which the chemical drug in interest is insoluble, but still miscible with the beverages tested (ii) then, adding a predefined volume of the drug-spiked beverage into a larger volume of the 'anti-solvent' leading to the formation of a colloidal-like turbid mixture which can be easily detected by simple optical means. The 'turbidity' effect leads to clear-cut optical changes and enhanced scattering of light, thus allowing the detection of drugs in spiked beverages. A general schematics for the solvent-anti-solvent detection approach of chemical drugs spiked in beverages is described FIG. 2.

First, the detection of GHB was experimented, as the most widely used chemical in drug-facilitated assaults. The practical GHB concentration ranges to be detected, for a 200 ml drink, are summarized in Table 1.

TABLE 1

The practical GHB concentration ranges to be detected for a 200 ml drink.

| GHB Dose (grams/100 ml) | GHB Percent in Drink | Physical Effect |
|---|---|---|
| <1 gram (low) | <1% | Mild relaxant |
| 1-2 grams (moderate) | 1-2% | Strong mental and physical relaxation |
| 2-4 grams (high) | 2-4% | Pronounce interference with motor control and speech and sleepiness. Deep sleep state (death danger) |
| 4-8 (very high) | 4-8% | Powerful deep sleep. 'Comatose' state (death danger) |

After extensive screening experiments, it was found that acetonitrile and pure ethanol were the best candidates for the detection of GHB spiked into a broad spectrum of alcoholic and non-alcoholic beverages, using the solvent (the beverage itself)-anti-solvent detection scheme. GHB was shown to be mostly insoluble in these solvents (anti-solvents), precipitating or leading to turbid colloidal solutions after the addition of GHB, FIG. 3. A large spectrum of GHB-spiked alcoholic beverages was tested, by adding a small volume of a spike beverage into a larger volume of the anti-solvent (1:10 volume ratio between the solvent and anti-solvent components, respectively). FIGS. 4A and B show the visual results of the acetonitrile anti-solvent solution, before and after the addition a clean vodka sample and a GHB-spiked vodka sample respectively, 10 mg/ml GHB (100 µl of beverage sample in a 1 ml anti-solvent volume). Evidently, the acetonitrile anti-solvent clear solution turned turbid immediately after the addition of a small volume of a GHB-spiked beverage. This dramatic effect was clearly detected by visual examination at concentrations of 10 mg GHB per ml beverage. Additional alcoholic beverages showed a similar effect, FIGS. 4C and 4D. This approach allowed the detection of GHB in a broad range of GHB concentration, with a detection limit of ~0.2-0.4 g GHB per 100-120 ml of beverage. This lowest limit of detection was considerably lower than the lowest GHB concentration required for sedation. Thus, the herein disclosed approach can be safely and reliably used to detect GHB spiked in beverages very rapidly without the risk of false-negative results as a result of low concentrations of GHB. Non-alcoholic light drinks, such as Coca Cola, light alcoholic drinks, such as wines and mixtures, such as cocktails did not lead to the observed results when using acetonitrile as an 'anti-solvent'. Notably, using pure ethanol as an anti-solvent for GHB detection in soft drinks, cocktails non-alcoholic drinks and light alcoholic drinks leads to similar results are those shown before, FIGS. 5A and B. Nevertheless, this difference in the anti-solvent agents for different beverages groups should not be regarded as a problem for the detection purposes, since the sensing can be easily performing using a multi-compartment device and sample splitting, FIG. 5C, as currently developed.

Figure 6B:
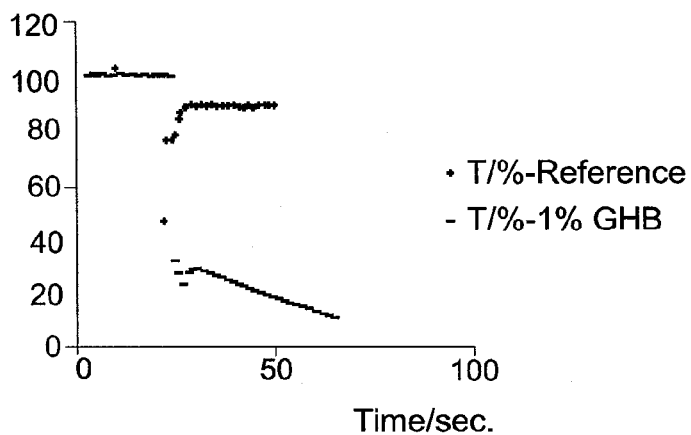

In order to reliably detect the presence of GHB in spiked drinks of different nature and to be able to quantify its detection, a device was constructed for allowing the changes in optical properties of the anti-solvent volume upon addition of small volumes of beverages under studies. This device consists on (i) sample holder, (ii) light source, (iii) light detector, (iv) electronics board and software, as shown in FIG. 6A. This device allows the simple and real-time rapid monitoring of light scattering changes, or obstruction of light path by the turbidity effect, caused by the presence of GHB in the tested spiked beverages. FIG. 6B shows the optical curves obtained from tests performed on a clean vodka sample, curve a, and on GHB-spiked vodka sample, curve b, using our newly developed device. As observed, the addition of a small volume of a GHB-free drink sample into the anti-solvent solution does not yield any optical changes in comparison to the baseline values observed on the clean anti-solvent. In comparison, GHB-spiked solutions led to clear abrupt and fast optical changes. This device allowed for the highly sensitive sensing of GHB in beverages, at concentrations much lower than those usually required in crime scene cases. The detection of GHB in beverages was clearly concentration dependent; higher GHB concentrations leading to higher and more evident optical changes. This clearly proves that the optical effects observed are a result of the addition of GHB into the tested drinks.

Figure 6C:
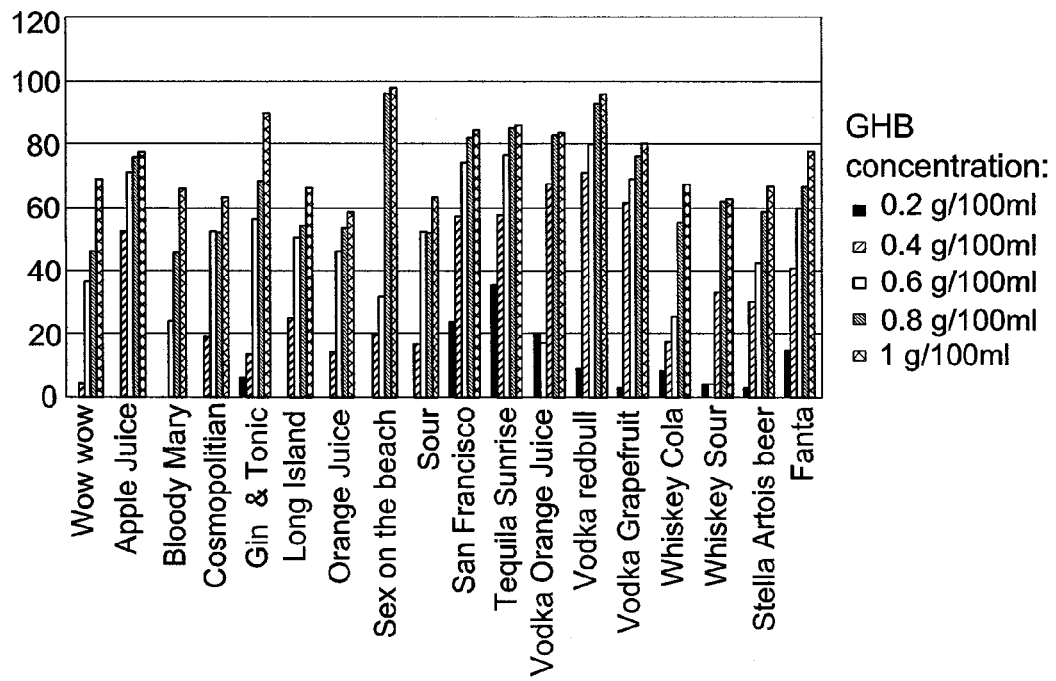

Numerous popular cocktail mixtures were tested as well, showing clear-cut optical changes after the addition of GHB, FIG. 6C. Notably, the methodology disclosed herein permits the reliable, ultrafast and sensitive detection of GHB in spiked drinks, regardless the composition of the beverages, their color, pH, density, etc.

In addition to GHB, other drugs such as ketamine are popular chemicals used in drug-facilitated sexual assault.

In order to prove the generality of the approach, modified methodology were tested to allow the detection of ketamine in drinks, at the relevant required concentrations. Active concentrations of ketamine to achieve sedative disabling effects are considerably lower than those used for GHB. In a 100 ml drink, the typical ranges of ketamine doses are outlined in Table 2.

TABLE 2

Typical ranges of ketamine doses in a 100 ml drink.

| Ketamine Dose (grams/100 ml) | Ketamine Percent in Drink | Physical Effect |
|---|---|---|
| 10-80 mg (low) | <0.01-0.08% | Mild euphoria |
| 80-130 mg (medium) | 0.08-0.13% | Disconnection from surroundings, loss of coordination |
| 130-250 mg (high) | 0.13-0.25% | K-hole, near comatose state |
| >250 mg (mega) | >0.25% | Powerful deep sleep. 'Comatose' state (death danger) |

Figure 7A:
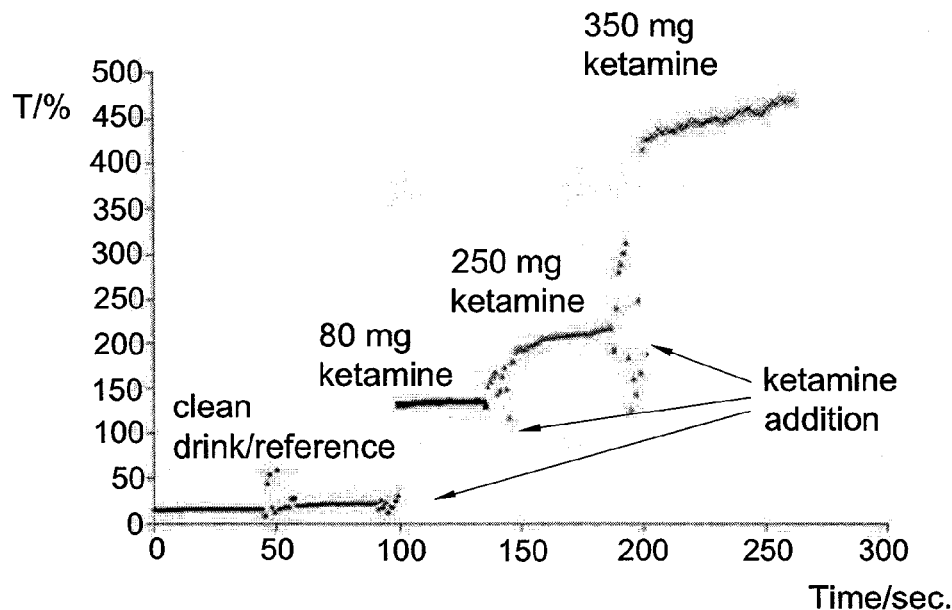
FIGS. 7A-B depict the results obtained with GHB-detecting experiments.
Figure 7B:
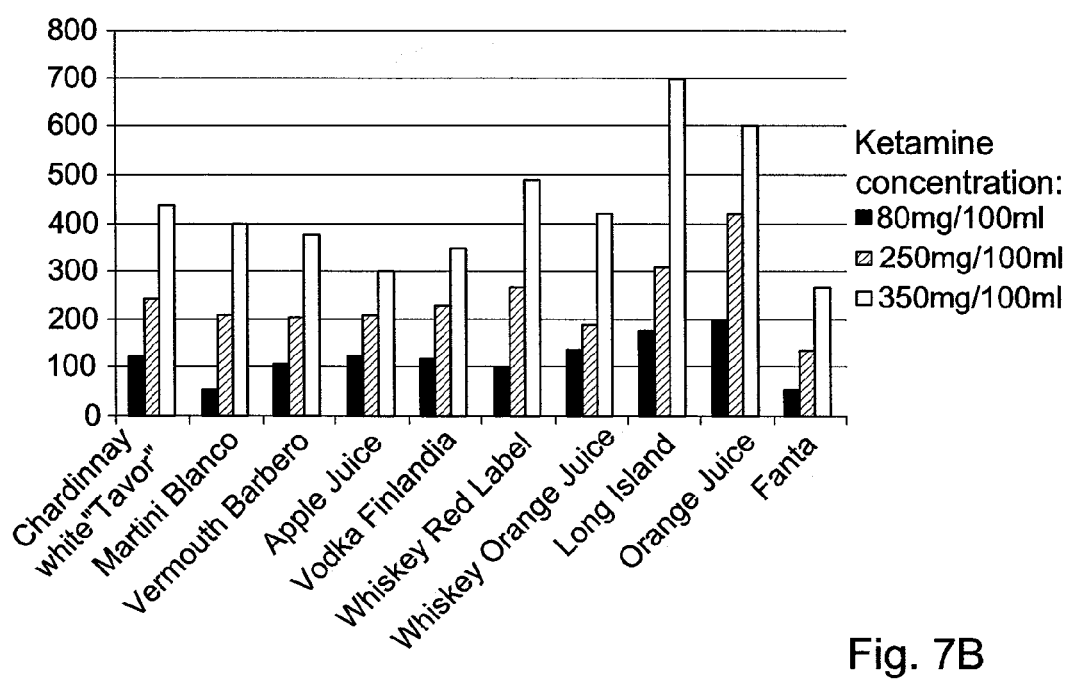

Systematic screening for potential test solution candidates showed that a isopropanol:glycerin:NaOH (1:10:0.25) mixture, a turbid solution, was a suitable candidate for the optical detection of ketamine-spiked beverages. In this case, the addition of a small volume of a ketamine-spiked beverage into the initially turbid testing solution led to an increased transmission (solution transparency increases) readily detected by a device of the invention, FIG. 7A. The detection of ketamine was readily performed in a broad range of beverages and was dependent on the concentration of ketamine under test, FIG. 7B.

Methods

The method is based on turbidity appearance in case of spiked drink (clean drink-transparent testing mixture, spiked-turbid).

Example 1

GHB Detection in High Alcohol Percentage Beverages

GHB was detected in two different methods:

1. A sample of a beverage was dissolved in Acetonitrille in a ratio 1:10 (Sample:MeCN). In the presence of GHB, at a concentration above 0.2 g/100 ml, the final solution turned colloid and the change was measured by light scattering. This method was useful for beverages containing 30% and higher alcohol.

2. A sample of a beverage was dissolved in an additional mixing substance containing a non-alcoholic soft drink or a low alcoholic mixture, such as Martini/Vermouth/other, in a ratio 1:1 (Sample: dissolving solution) and the newly formed solution was dissolved in EtOH, Abs 96%, in a ratio 1:10. In the presence of GHB at a concentration above 0.4 g/100 ml, the final solution turned colloid/turbid and the change was measured by a light scattering or any other turbidimetric method. This method was useful for testing drug content in any soft drink-from to highly alcoholic.

As an alternative the mixing substance (soft or low-alcohol % containing drink) can be combined with a testing solvent (EtOH) in a ratio from 1:10 to 1:20 (mixing substance:EtOH). Results are the same.

Example 2

GHB Detection in Low Alcohol Percentage Beverages, Cocktails and Non-alcoholic Drinks GHB such drinks can be detected either by method 2 of Example 1 above or by the following method.

A sample of a beverage was dissolved in EtOH, Abs 96%, in a ratio 1:10 (Sample:EtOH). In the presence of GHB at a concentration above 0.2 g/100 ml, the final solution turned colloid and a change was measured by a light scattering.

In a device for GHB detection 2 sample chambers are constructed: one for detection in highly alcoholic drinks and another for all other drinks.

Ketamine

The method is based on transparency rising, from initially turbid mixing testing solution, in case of spiked drink.

Example 3

Ketamine Detection in All Kinds of Beverages

A sample of a beverage/drink was dissolved in a testing reagent, which consisted of isopropyl alcohol (IPA), NaOH and Vermouth, at a ratio of 1:10 (Vermouth:IPA+0.001M NaOH). This solution was colloidic (clowdy/turbid) from the beginning. In case of beverage being ketamine free the colloid will remain. In the presence of ketamine in relevant concentrations (80 mg-400 mg), the transparency of a final solution increased.

Example 4

Ketamine Detection in Low Alcohol Percentage Beverages, Cocktails and Non-alcoholic Drinks Ketamine in such drinks was detected either by the method of Experiment 3 or by the following method.

A sample of a beverage was dissolved in IPA+0.001M NaOH solution in a ratio 1:10. In a "ketamine-free" drink, a colloid appeared. In the presence of ketamine in relevant concentrations, the transparency of a final solution increased.

The optical change observed for GHB detection is quite different from that observed for ketamine. In ketamine detection the colloid structure is formed with a "clean" drink and disappears upon the addition of ketamine. This difference clearly has no effect on the measurable optical parameters.

Example 5

Blind Test Summary

A series of beverages and random mixtures thereof have been randomly spiked with GHB. The beverages were tested without prior knowledge of their composition, i.e., present of GHB. GHB concentrations were about 1 g/120 ml.

The selection of beverages included known beverages and randomly prepared drinks (e.g., mixtures of popular cocktails).

Table 3 below summarizes the composition of each sample.

TABLE 3

A summary of tested beverages, with and without GHB.

| Sample number | Sample composition | Presence of GHB | Result authentication |
|---|---|---|---|
| 1 | Vermouth | + | V |
| 2 | Finish vodka | X | — |
| 3 | Martini | X | — |
| 4 | Finish vodka | X | — |
| 5 | Martini | + | V |
| 6 | Vermouth | X | — |
| 7 | Finish vodka | X | — |
| 8 | Finish vodka | + | V |
| 9 | Finish vodka | X | — |
| 10 | Sour | + | V |
| 11 | Scotch whiskey | + | V |
| 12 | Martini | X | — |
| 13 | Vermouth | X | — |
| 14 | Red wine | + | V |
| 15 | Finish vodka | + | V |
| 16 | Red wine + Martini | + | V |
| 17 | White wine | X | — |
| 18 | Finish vodka | X | — |
| 19 | Vermouth | + | V |
| 20 | Finish vodka | X | — |
| 21 | Red wine | X | — |
| 22 | Red wine | X | — |
| 23 | Red wine | + | V |
| 24 | Red wine | X | — |
| 25 | Orange juice | X | — |
| 26 | Finnish vodka + orange juice | + | V |
| 27 | Fanta | + | V |
| 28 | Fanta | X | — |
| 29 | Fanta | + | V |
| 30 | Sprite | + | V |

TABLE 3-continued

A summary of tested beverages, with and without GHB.

| Sample number | Sample composition | Presence of GHB | Result authentication |
|---|---|---|---|
| 31 | Sprite | X | — |
| 32 | Martini + Tonic | + | V |
| 33 | Martini + Tonic | X | — |
| 34 | Apple juice + pomegranate juice | X | — |
| 35 | Pomegranate juice | + | V |
| 36 | Apple juice + pomegranate juice | + | V |
| 37 | Orange juice | + | V |
| 38 | Orange juice | X | — |
| 39 | Sprite + apple juice | + | V |
| 40 | Sprite + apple juice | X | — |
| 41 | Vodka + graipfruit juice | + | V |
| 42 | Vodka + grapefruit juice | X | — |
| 43 | Vodka + graipfruit juice | X | — |
| 44 | Coca-Cola | + | V |
| 45 | Coca-Cola | X | — |
| 46 | Vodka + Coca-Cola | X | — |
| 47 | Tequila | X | — |
| 48 | Tequila | X | — |
| 49 | Jin and Tonic | + | V |
| 50 | Jin and Tonic | X | — |
| 51 | Orange Juice | + | V |
| 52 | Tequila | + | V |

In the Table: + indicates a GHB-spiked beverage; X indicates "clean" (unspiked) beverage; V indicates successful detection of a drug-spiked beverage; — indicates successful determination that the beverage is GHB-free.

As may be noted from Table 3, in all 52 tested beverages the presence or absence of GHB was efficiently determined by the employing the process of the invention. No false positives were produced.

A similar test was conducted for Ketamine with similar results.

The invention claimed is:

1. A method for determining the presence/absence of a drug in a liquid medium, the method comprising:
providing one or more solvent mixture(s) having a predetermined optical parameter, said solvent mixture(s) being capable of undergoing a change in at least one optical parameter in the presence of a drug; and
contacting said solvent mixture with a liquid medium sample suspected of containing an amount of said drug;
whereby a change in the predetermined optical parameter of said solvent mixture following the contacting thereof with said liquid medium sample, indicates the presence of said drug in said liquid medium,
wherein the change in the predetermined optical parameter being dependent on the full or partial insolubility of the drug in the solvent mixture.

2. The method according to claim 1, wherein the sample is allowed to mix with said solvent mixture so as to induce or hasten a change in said at least one optical parameter.

3. The method according to claim 1, wherein said drug is a recreational drug or an illicit drug.

4. The method according to claim 3, wherein said drug is selected from a depressant, an antihistamine, an analgesic, a tranquilizer, a hallucinogen, a psychedelic, a deliriant and a stimulant.

5. The method according to claim 1, wherein said drug is selected from amobarbital, aprobarbital, alphenal, barbital, brallobarbital, phenobarbital, alprazolam, bretazenil, bromazepam, brotizolam, chlordiazepoxide, cinolazepam, clonazepam, clorazepate, clotiazepam, cloxazolam, delorazepam, diazepam, estazolam, etizolam, flurazepam, flutoprazepam, halazepam, ketazolam, loprazolam, lorazepam, lormetazepam, medazepam, midazolam, nimetazepam, nitrazepam, nordazepam, oxazepam, phenazepam, pinazepam, prazepam, premazepam, quazepam, temazepam, tetrazepam, triazolam, ipratropium bromide, oxitropium bromide, tiotropium, glycopyrrolate, oxybutinin, tolterodine, azelastine cetirizine, cyclizine, chlorpheniramine, clemastine, desloratadine, dexchlorpheniramine, dimenhydrinate, dimetindene, diphenhydramine, doxylamine, ebastine, embramine, fexofenadine, levocetirizine, loratadine, meclozine, olopatadine, pheniramine, promethazine, quetiapine, rupatadine, cimetidine, famotidine, lafutidine, nizatidine, ranitidine, roxatidine, paracetamol, and non-steroidal anti-inflammatory drugs (NSAIDs).

6. The method according to claim 1, wherein said drug is selected from benzodiazepines, nonbenzodiazepines, carisoprodol, chloral hydrate, diethyl ether, ethchlorvynol, gabapentin, gamma-butyrolactone (GBL), gamma-hydroxybutyrate (GHB), glutethimide, kava, kavalactones meprobamate, methaqualone, pregabalin, propofol, theanine, valerian, atropine, dimenhydrinate, diphenhydramine, hyoscyamine, scopolamine, myristicin, ibotenic acid, muscimol, dextromethorphan, dextromethorphan, chlorpheniramine, ketamine, methoxetamine, phencyclidine, nitrous oxide, phenethylamines, MDMA, mescaline, tryptamines, alpha-methyltryptamine, bufotenin, dimethyltryptamine, lysergic acid amide, lysergic acid diethylamide, psilocin, psilocybin, ibogaine, salvinorin A, sympathomimetics, Entactogens, arecoline, rauwolscine and yohimbine.

7. The method according to claim 1, wherein said drug is selected from caffeine, tetrahydrocannabinol (THC), hydrocodone, oxycodone, morphine, diacetylmorphine, cocaine, lidocaine and novocaine.

8. The method according to claim 1, wherein said drug is selected from GHB or derivatives or prodrugs of GHB, and ketamine.

9. The method according to claim 1, wherein said liquid medium is water, an aqueous medium, an alcoholic medium or an organic medium.

10. The method according to claim 9, wherein said medium is a beverage.

11. The method according to claim 10, wherein said liquid medium is a beverage comprising water, or an alcoholic beverage or a non-alcoholic beverage or a soft drink, or a fruit juice, or a hot beverage.

12. The method according to claim 1, wherein said drug is GHB and the solvent mixture comprises acetonitrile and/or ethanol.

13. The method according to claim 1, wherein said drug is GHB and the solvent mixture is ethanol:acetonitrile or acetonitrile (100%) or ethanol (100%), or ethanol:acetonitrile (1:1) or isopropanol and/or glycerine and/or NaOH or isopropanol, glycerine and NaOH or isopropanol:glycerine:NaOH (1:10:0.25).

14. The method according to claim 1, wherein said at least one optical parameter is optical density.

15. A device for determining the presence of a drug in a liquid medium, the device comprising;
at least one testing cell for holding a solvent mixture,
means for withdrawing a liquid medium sample suspected of containing a drug into said at least one testing cell,
a detection unit for detecting a change in at least one optical parameter of the mixture in said testing cell following contact with said sample, and
optionally further comprising an indication unit in the form of a visual or an audio display, wherein the change in the at least one optical parameter being dependent on the full or partial insolubility of the drug in the solvent mixture.

16. The device according to claim 15, wherein said detection unit comprises a light source capable of generating a light beam of a predetermined wavelength, said beam being directed so as to pass through one or more testing cells, the testing cell(s) being suitable for holding a solvent mixture and a sample liquid medium suspected of containing a drug, the presence or absence of said drug being determined by at least one change in a predetermined optical parameter of said solvent mixture, said detection being carried out by a photodetector, and optionally, further comprising an inlet unit permitting communication of a sample into said testing cell(s) and/or a visual or audio indicator.

17. The device according to claim 16, wherein the predetermined wavelength is 450 nm and/or 560 nm and/or 750 nm.

18. The device according to claim 16, being operable in a transmittance measurement mode, whereby the photodetector is mounted along the incident beam axis or in a scattering measurement mode, whereby the photodetector is mounted perpendicular to the incident beam axis.

19. The device according to claim 16, being suitable for multiple and consecutive uses or multiple simultaneous uses.

20. The device according to claim 16, being in the form of or attached to a straw, a beverage stirring bar, a cutlery, a beverage coaster, a placemat, a pen, a liquid medium carrier, a glass of beverage, a cup, a bowl, a dish, a cocktail napkin, a menu, or a personal card.

* * * * *